United States Patent
Smith et al.

(10) Patent No.: US 7,588,029 B2
(45) Date of Patent: Sep. 15, 2009

(54) HUMIDIFIED GASES DELIVERY APPARATUS

(75) Inventors: Daniel John Smith, Auckland (NZ); Hussein Kadhum, Auckland (NZ); Malcolm David Smith, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 67 days.

(21) Appl. No.: 09/956,723

(22) Filed: Sep. 20, 2001

(65) Prior Publication Data

US 2002/0124847 A1 Sep. 12, 2002

Related U.S. Application Data

(63) Continuation-in-part of application No. 09/808,567, filed on Mar. 14, 2001, now Pat. No. 6,918,389.

(30) Foreign Application Priority Data

Mar. 21, 2000 (NZ) ........................ 503495

(51) Int. Cl.
*A61M 15/00* (2006.01)
*F24J 3/00* (2006.01)
(52) U.S. Cl. ............................ 128/203.17; 128/203.23; 128/203.27; 128/204.17
(58) Field of Classification Search ............ 128/203.16, 128/203.17, 203.26, 204.14, 204.18, 203.12, 128/911, 912, 200.14, 200.24, 203.14, 203.27, 128/204.17, 204.21, 207.14–207.18; 392/311, 392/314–338, 341–346, 350, 360, 386, 394, 392/396–398, 478–494; 338/22 R, 23, 22 SD; 219/200, 236, 237, 238, 239, 502
See application file for complete search history.

(56) References Cited

U.S. PATENT DOCUMENTS

| 485,127 | A | 10/1892 | Lynch |
|---|---|---|---|
| 3,243,753 | A | 3/1966 | Kohler |
| 3,582,968 | A | 6/1971 | Buiting |
| 3,584,193 | A | 6/1971 | Badertscher |
| 3,695,267 | A | 10/1972 | Hirtz et al. |
| 3,766,914 | A | 10/1973 | Jacobs |
| 3,823,217 | A | 7/1974 | Kampe |
| 3,914,349 | A | 10/1975 | Stipanuk |
| 4,013,122 | A | 3/1977 | Long |
| 4,013,742 | A | 3/1977 | Lang |

(Continued)

FOREIGN PATENT DOCUMENTS

DE 3311811 10/1983

(Continued)

*Primary Examiner*—Steven O Douglas
*Assistant Examiner*—Brian Won
(74) *Attorney, Agent, or Firm*—Trexler, Bushnell, Giangiorgi, Blackstone & Marr, Ltd.

(57) ABSTRACT

A gases transportation pathway for use in supplying a humidified gases stream to a patient includes regulated conduit heating. The regulated conduit heating may include a section of positive temperature coefficient material wherein the localized electrical resistance of the material is positively related to the localized temperature. The regulated conduit heating may be a layer of positive temperature coefficient material within the wall of the gases transportation pathway with at least a pair of conductors running the length of the pathway and in electrically conductive contact with the positive temperature coefficient material.

7 Claims, 6 Drawing Sheets

U.S. PATENT DOCUMENTS

| | | | |
|---|---|---|---|
| 4,038,980 A | | 8/1977 | Fodor |
| 4,060,576 A | | 11/1977 | Grant |
| 4,110,419 A | | 8/1978 | Miller |
| 4,172,105 A | | 10/1979 | Miller et al. |
| 4,177,376 A | * | 12/1979 | Horsma et al. ............... 219/553 |
| 4,459,473 A | * | 7/1984 | Kamath ....................... 219/553 |
| 4,500,480 A | | 2/1985 | Cambio, Jr. |
| 4,543,474 A | | 9/1985 | Horsma et al. |
| 4,560,498 A | | 12/1985 | Horsma et al. |
| 4,574,188 A | | 3/1986 | Midgley et al. |
| 4,640,804 A | | 2/1987 | Mizoguchi |
| 4,676,237 A | | 6/1987 | Wood et al. |
| 4,684,786 A | | 8/1987 | Mann et al. |
| 4,710,887 A | | 12/1987 | Ho |
| 4,722,334 A | | 2/1988 | Blackmer et al. |
| 4,753,758 A | | 6/1988 | Miller |
| 4,780,247 A | | 10/1988 | Yasuda |
| 4,791,966 A | | 12/1988 | Eilentropp |
| 4,808,793 A | * | 2/1989 | Hurko ......................... 392/489 |
| 4,829,998 A | | 5/1989 | Jackson |
| 4,911,157 A | | 3/1990 | Miller |
| 4,911,357 A | | 3/1990 | Kitamura |
| 4,921,642 A | | 5/1990 | LaTorraca |
| 4,941,469 A | | 7/1990 | Adahan |
| 5,031,612 A | | 7/1991 | Clementi |
| 5,062,145 A | | 10/1991 | Zwaan et al. |
| 5,092,326 A | | 3/1992 | Winn et al. |
| 5,101,820 A | | 4/1992 | Christopher |
| 5,148,801 A | | 9/1992 | Douwens et al. |
| 5,224,923 A | | 7/1993 | Moffett et al. |
| 5,231,979 A | | 8/1993 | Rose et al. |
| 5,336,156 A | | 8/1994 | Miller et al. |
| 5,346,128 A | | 9/1994 | Wacker |
| 5,367,604 A | * | 11/1994 | Murray ....................... 392/394 |
| 5,388,443 A | | 2/1995 | Manaka |
| 5,392,770 A | | 2/1995 | Clawson et al. |
| 5,404,729 A | * | 4/1995 | Matsuoka et al. ............. 62/179 |
| 5,454,061 A | | 9/1995 | Carlson |
| 5,482,031 A | | 1/1996 | Lambert |
| 5,516,466 A | | 5/1996 | Schlesch et al. |
| 5,529,060 A | | 6/1996 | Salmon et al. |
| 5,558,084 A | | 9/1996 | Daniell et al. |
| 5,564,415 A | | 10/1996 | Dobson et al. |
| 5,588,423 A | | 12/1996 | Smith |
| 5,640,951 A | * | 6/1997 | Huddart et al. ........ 128/204.17 |
| 5,673,687 A | | 10/1997 | Dobson et al. |
| 5,705,555 A | | 1/1998 | Guilfoy et al. |
| 5,759,149 A | | 6/1998 | Goldberg et al. |
| 5,769,071 A | | 6/1998 | Turnbull |
| 5,988,164 A | | 11/1999 | Paluch |
| 5,991,507 A | | 11/1999 | Bencsits |
| 6,024,694 A | | 2/2000 | Goldberg et al. |
| 6,050,260 A | | 4/2000 | Daniell et al. |
| 6,078,730 A | | 6/2000 | Huddart et al. |
| 6,090,313 A | | 7/2000 | Zhao |
| 6,095,505 A | | 8/2000 | Miller |
| 6,125,847 A | | 10/2000 | Lin |
| 6,158,431 A | | 12/2000 | Poole |
| 6,311,958 B1 | | 11/2001 | Stanek |
| 6,349,722 B1 | * | 2/2002 | Gradon et al. ......... 128/203.17 |
| 6,367,472 B1 | | 4/2002 | Koch |
| 6,394,084 B1 | | 5/2002 | Nitta |
| 6,397,846 B1 | | 6/2002 | Skog et al. |
| 6,398,197 B1 | | 6/2002 | Dickinson et al. |
| 6,463,925 B2 | | 10/2002 | Nuckolas et al. |
| 6,474,335 B1 | | 11/2002 | Lammers |
| 6,543,412 B2 | * | 4/2003 | Amou et al. ................ 123/337 |
| 6,564,011 B1 | | 5/2003 | Janoff et al. |
| 6,694,974 B1 | | 2/2004 | George-Gradon et al. |
| 6,718,974 B1 | | 4/2004 | Moberg |
| 6,918,389 B2 | | 7/2005 | Seakins et al. |
| 7,120,354 B2 | | 10/2006 | Mackie et al. |
| 2002/0124847 A1 | | 9/2002 | Smith et al. |
| 2002/0186966 A1 | * | 12/2002 | Zimmer et al. .............. 392/397 |

FOREIGN PATENT DOCUMENTS

| | | |
|---|---|---|
| DE | 3629353 | 1/1988 |
| DE | 4034611 | 5/1992 |
| DE | 94092311 | 11/1994 |
| EP | 0258928 | 9/1988 |
| EP | 0 356 000 | 2/1990 |
| EP | 481459 | 4/1992 |
| EP | 0556561 | 8/1993 |
| EP | 0 616 166 | 9/1994 |
| EP | 0672430 | 9/1995 |
| EP | 0885623 | 12/1998 |
| EP | 1138341 | 10/2001 |
| EP | 0556561 | 8/2003 |
| GB | 1167551 | 10/1969 |
| GB | 2277689 | 11/1994 |
| JP | 05317428 | 12/1993 |
| JP | 08061731 | 8/1996 |
| JP | 09234247 | 9/1997 |
| JP | 2001-129091 | 5/2001 |
| SU | 379270 | 4/1973 |
| WO | WO 9826826 | 6/1998 |
| WO | WO 0110489 | 2/2001 |
| WO | WO02/32486 | 4/2002 |
| WO | WO 02/32486 | 4/2002 |

* cited by examiner

HUMIDIFIED GASES DELIVERY APPARATUS

This application is a continuation-in-part application of Ser. No. 09/808,567, filed on Mar. 14, 2001 now U.S. Pat. No. 6,918,389 and entitled Breathing Assistance Apparatus.

BACKGROUND TO THE INVENTION

1. Field of the Invention

The present invention relates to apparatus for the delivery of humidified gases and in particular to conduits for humidified breathing circuits.

2. Summary of the Prior Art

A number of methods are known in the art for supplying humidified gases to a patient requiring breathing assistance. Such prior art humidifiers generally comprise a source of pressurised air (or other mixture of gases), a humidification chamber including a source of water and a heating means to vaporise the water, and a conduit to convey the humidified gases to the patient or user.

For example U.S. Pat. No. 4,038,980 describes a "flash vaporisation" humidifier where water drips onto a low thermal mass heater to create respiratory humidity. It mentions "control means may be provided automatically to regulate the water supply rate in response to means sensing the relative humidity", however they prefer a manual control of water flow rate. Thus it incorporates a humidity sensor and controls the water rate, as opposed to controlling the amount of electrical heating.

U.S. Pat. No. 5,092,326 also describes the use of a humidity sensor in a humidifier. It describes a high frequency ventilation system that incorporates a heated humidifier and a humidity sensor, where these are linked to a central microprocessor. Apparatus is disclosed to moisten a gas mixture supplied to the airway, and a microprocessor controls the amount of moisture supplied to the gas mixture.

U.S. Pat. No. 5,769,071 describes a humidifier incorporating a heat and moisture exchanger (HME), supply of water to the HIE, heater element and humidity sensor. The humidity sensor can control humidity via water supply rate or temperature (via the heater element). The humidity sensor is described as being at the patient airway.

U.S. Pat. No. 5,988,164 describes a heated breathing tube system for use with a humidifier. This uses a relative humidity sensor (located near the patient) to control the amount of heating provided by the heated breathing circuit so that the gas is at a constant level of relative humidity. The heated breathing circuit may use either electrical heating, or heating via warm recirculating water in a tube. Also described is a method of control of the electric heater wire or heated water tube based on the output of relative humidity sensor.

The previously mentioned U.S. Pat. Nos. 4,038,980 and 5,769,071 both describe humidifiers where the humidification chamber is located close (proximal) to the patient. These have the disadvantage of introducing weight, heat and complexity near the patient which is inconvenient and could be painful to the patient. Of the cited prior art only U.S. Pat. No. 5,988,164 specifically describes the humidification chamber as being located remotely from the patient.

There are several disadvantages of the prior art systems using a humidification chamber located remotely from the patient. It is normally assumed that gases leaving such prior art humidifiers are saturated with water vapour (100% relative humidity). However there is no guarantee that the gases leaving such humidifiers are in fact saturated with water vapour. In certain circumstances (e.g. with the incoming air already warm), the gases leaving such humidifiers can be significantly less than 100% relative humidity. This is because the humidifiers are typically controlled to achieve a desired outlet gas temperature, which in some cases may not be much more than the incoming air.

Another drawback of the prior art systems is that condensation can occur in the (sometimes heated) conduits connecting the patient to the respiratory assistance equipment. This may occur if the temperature profile along such conduits is not even and allows some parts of the conduit to be colder than the gas at these points.

A third disadvantage of such prior art systems is that where the gas leaving the humidifier is at 100% relative humidity. It must be heated immediately by some form of conduit heater or it may lose heat through the walls of the conduit otherwise condensation and therefore a drop in the amount of absolute humidity contained in the gas will result.

Another, fourth, disadvantage of the prior art systems is the need for a sensor very near to the patient, which adds to the weight and bulk of equipment at the patients airway.

SUMMARY OF THE INVENTION

It is therefore an object of the present invention to provide apparatus for the delivery of humidified gases which goes some way to overcoming the above mentioned disadvantages.

Accordingly in a first aspect the present invention consists in a humidification apparatus for providing a humidified gases flow to a patient or other person in need of such gases comprising:

humidification chamber means, having an inlet and an outlet to allow said gases flow to pass through said humidification chamber means, chamber heating means provided adjacent said humidification chamber means and adapted to vaporise liquid water in said humidification chamber means in order to provide water vapour to said gases flow passing through said humidification chamber means, gases transportation pathway connected to said outlet of said humidification chamber means to convey said gases flow to said patient or other person in need of such gases, and self-regulated conduit heating means adapted to regulate the temperature profile of said gases flow along said gases transportation pathway and/or of said gases transportation pathway, to substantially coincide with a predetermined profile.

In a further aspect the present invention consists in a gases transportation pathway for transporting humidified gases to a patient, said pathway comprising:

an enclosing wall including at least a layer of positive temperature co efficient material wherein the localised electrical resistance of said material is positively related to the localised temperature, and at least two electrical conductors running the length of said pathway and disposed an electrical contact with said positive temperature co efficient material.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings.

DETAILED DESCRIPTION OF THE PREFERRED EMBODIMENTS

Figure 1:
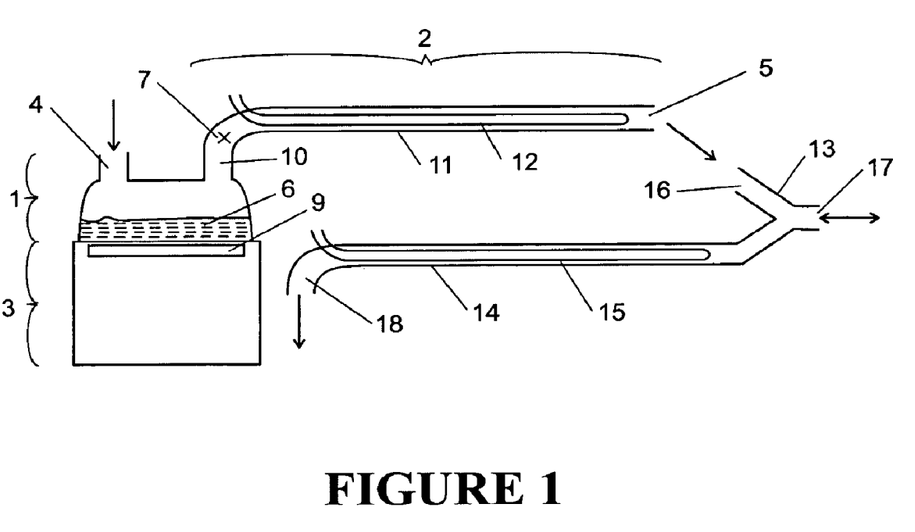
FIG. 1 shows an example of an humidification system, with three basic parts
Figure 2:
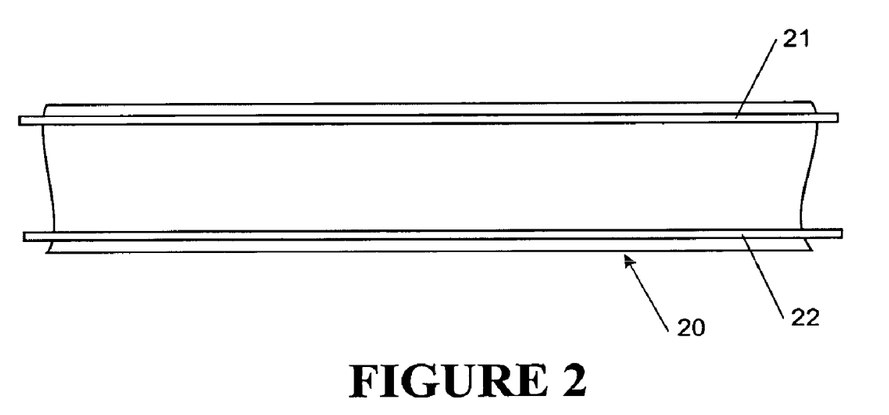
FIG. 2 is a plan view of a section of a ribbon of PTC material with an electrode embedded along each edge.

FIG. 1 illustrates a typical respiratory humidification system, comprised of three parts:

1) a humidification chamber located at a distance from the patient, which heats and substantially saturates gases flowing through it;

2) a delivery system consisting of a flexible tube which carries humidified gases from the humidification chamber 1 to the gas outlet 5; and 3) a heater base which heats the humidification chamber 1 and provides measurement and control functions.

The gas to be humidified flows into the chamber 1 from port 4 and leaves the delivery system 2 at gas exit port 5. Gas from exit port 5 flows to a patient via a face mask or similar (not shown). Dry gases at the gas input 4 are heated and humidified by passing over the surface of hot water 6 in the chamber 1 so that they are substantially saturated with water vapour when they leave chamber 1 at exit port 10. Hot water 6 is heated by heater plate 9 and the amount of heating is controlled so that the gas reaches a predetermined temperature at exit port 10. Therefore the humidification chamber 1 acts to heat and humidify the medical gases so that they are substantially saturated at the output of chamber 1, and are at a predetermined temperature.

The gas delivery system 2 (also known as a delivery tube or breathing circuit) consists of a flexible tube 11 containing a heater 12. The gas from the humidification chamber 1 passes through the tube 11 and is heated by heater 12 to offset heat losses through the walls of tube 11.

The system as described has gas entering gas inlet 4 from a continuous flow gas source (not shown) and exiting the system through gas outlet 5. However the system is equally applicable where the gas source is a ventilator, which creates intermittent flow patterns to provide breaths to a patient. In this case gas outlet port 5 is connected directly to gas inlet port 16. The patient is connected to port 17 via an endotracheal tube, mask, mouthpiece or other patient interfaces (not shown). During patient inspiration dry gases from the ventilator enter the system at inlet port 4, pass through chamber 1, delivery system 2, pass through wye-piece 13 and reach the patient through port 17. During patient exhalation gases pass back through port 17, through wye-piece 13, tube 14 and leave through gas outlet port 18. Tube 14 may also be heated by heater 15 to prevent condensation.

One aspect of the present relates to removing the need for a sensor at the patient airway. To remove this sensor safely, we must be certain that the gas entering the delivery tube has a safe level of temperature and absolute humidity, and that the surfaces inside the delivery tube do not exceed safe temperature levels. This implies a delivery tube that has a constant internal wall temperature.

It would be desirable, therefore, to have a heated delivery tube which self-regulates its temperature at a desired level. The heater could either be embedded in the wall of the delivery tube itself, or it could lie inside the lumen of the delivery tube, or it could be wrapped around the outside of the delivery tube. Such a heater could be made from positive temperature coefficient (PTC) material (such as "Winterguard" from Raychem Corp., Menlo Park, Calif. USA), so that the resistance of the heater increases if the heater is hot, resulting in reduced power. However the delivery tube may pass trough more than one environment, or may have localised drafts present on certain parts of the tube. If the PTC elements are arranged in parallel, then the full benefit of the PTC heater can be envisaged. If the PTC elements are arranged in parallel, then the cold portions of the tube will have a lower resistance, which will result in more heat being dissipated. Thus the tube will tend to regulate its own temperature.

Figure 10:
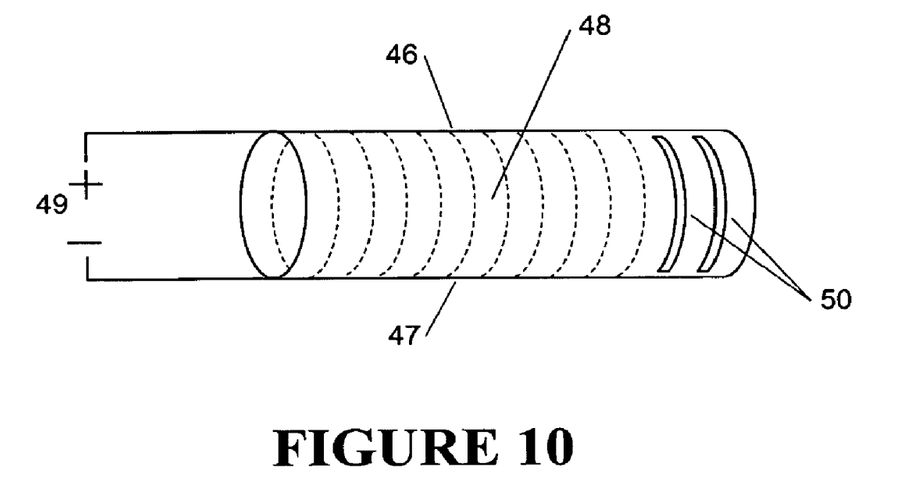
FIG. 10 shows construction of a tube incorporating flexible PTC elements in a parallel wire configuration.

FIG. 10 shows constriction of a tube incorporating flexible PTC elements in a parallel wire configuration. The tube 48 is made of a flexible PTC material, which has two low resistive strip connections, 46 and 47, on either side of it. This allows each portion of the tube to consist of short conducting segments of tube connected in parallel between conductors 46 and 47. These segments are represented by dotted lines encircling the tube in FIG. 10. The conductors 46 and 47 are connected to adjustable voltage source 49, which may be AC or DC. The tube would have an outer layer (not shown) which provides electrical insulation and thermal insulation to the tube. Each longitudinal segment of the tube will be able to regulate its own temperature independently of the rest of the tube.

Although one specific PTC heated tube design has been envisaged and described, other PTC tube designs could be used. Some additional tube designs are described out below. It may also be of advantage to create a PTC tube that has a differing temperature profile along its length rather than a constant temperature profile. The PTC design could also be extended to incorporate PTC heaters in other parts of the patient breathing circuit, such as the flexible extension tube which is usually connected between the Y-piece port 17 of FIG. 1) and the patient's endotracheal tube. A further extension of the PTC tube concept would be into a self-heated and temperature controlled endotracheal tube.

Figure 11:
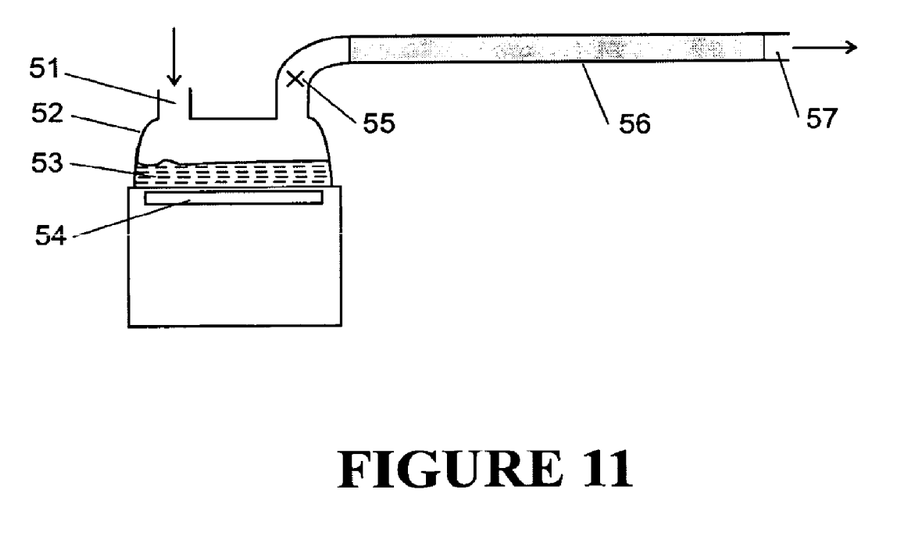
FIG. 11 shows a humidifier configuration using the tube in any one of FIGS. 8 to 10.

The PTC tube described with reference to FIG. 10 allows us to create a humidifier which doesn't use any sensor at the patient airway. FIG. 11 shows a humidifier configuration using this tube. Gas enters humidification chamber 52 via inlet port 51 and is humidified by water 53, heated by heater plate 54. Absolute humidity sensor 55 controls the heater plate so that the gas passing sensor 55 is at a desired level of absolute humidity. PTC tube 56 is heated by an external voltage (not shown) so that the internal surface temperature is at a constant desired temperature, which is selected to be above the dewpoint of the gas. The gas which leaves tube 56 at outlet 57 will therefore be near the temperature of the tube, and containing the desired level of absolute humidity which was controlled by absolute humidity sensor 55.

A variation of the system shown in FIG. 11 would be to use a temperature sensor at position 55. Another variation of a tube with a constant internal wall temperature would a delivery tube with heated water or other fluid pumped through smaller conduits in the wall of the delivery tube. Since the heated fluid has a high specific heat relative to air, the temperature of the fluid remains fairly constant during passage through the delivery wall conduits.

Referring to FIGS. 2 to 8 further preferred forms of the present invention are described. These forms provide a heated delivery tube which self-regulates its temperature at a desired level. The heater may be embedded in the wall of the delivery tube itself, form the fabric of the tube or lie inside the lumen of the delivery tube. The heater of the present invention is formed from a positive temperature coefficient (PTC) material.

The resistance of a PTC material increases markedly once it reaches a threshold temperature, resulting in reduced power consumption and subsequent cooling. The delivery tube may pass through more than one environment, or may have localised drafts present on certain parts of the tube.

In one embodiment of the present invention the PTC heater is provided as an elongate structure laying within the lumen of the delivery tube. The construction according to a preferred embodiment is illustrated with respect to FIGS. 2 to 4. In particular the heater structure is formed from a ribbon 20 of PTC plastic material adjacent with conductors 21, 22 embedded in the plastic material adjacent the opposite edges thereof. In use the conductors are attached to a power supply to provide a voltage difference between the conductors and cause a current to flow between them depending on the resistance of the PTC material.

Figure 3:
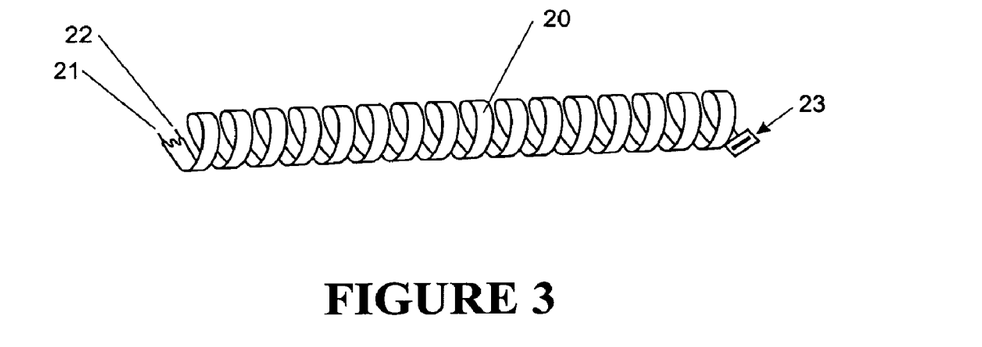
FIG. 3 is a plan view of a spirally configured heater element using the PTC ribbon of FIG. 2.
Figure 4:
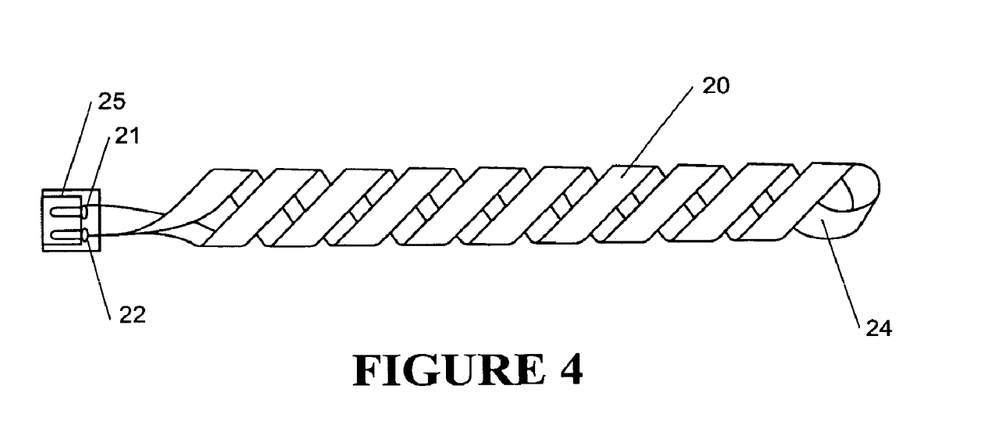
FIG. 4 is a plan view of a second form of spirally configured PTC ribbon heater element.

The ribbon may be provided in the tube as a single length of ribbon blindly terminated at one end and terminated with a power connector at the other end. This configuration is illustrated in FIG. 3 where the ribbon 20 is wound into a generally helical configuration and is terminated at one end with a blind connector 23. Termination of the other end at a power connector is not shown. In a alternative configuration the ribbon may be provided as a loop so that both ends terminate at the power connector with both ends of the positive electrode terminating at the positive pin and both ends of the negative or ground electrode terminating at the ground and negative pin. This configuration is depicted in FIG. 4, in which the ribbon 20 is provided in a generally double helical configuration. The conductors 21 and 22 have both ends terminating in the power connector 25 at one end of the heater structure. The ribbon 20 loops back upon itself at the other end 24 of the heater structure.

With the pair of conductors provided along opposite edges of the ribbon the PTC material offers an amorphous array of parallel current paths along the entire length of the ribbon. Where the internal conduit temperature is lower the heater structure will have a lower resistance and more current will flow producing a greater heater effect. Where the internal temperature in the conduit is higher the PTC material will have a higher resistance, choking off current flow and reducing heating in that region of the conduit.

In a further aspect of the invention the PTC material is arranged in a parallel circuit over the length of the tube and forming part of the wall itself the fall benefit of using PTC heater can be obtained. At the cold portions of the tube the material will have a lower resistance, which will result in more heat being dissipated in that area. Thus the tube will tend to regulate its own temperature.

In particular if the PTC material is composed to provide a threshold temperature at or just above the preferred gases temperature (eg above the dew-point of the humidified gases) the PTC material will maintain itself at that threshold temperature (with some hysteresis fluctuation) and condensation on the conduit surface will be at least substantially eliminated. This provides effective condensation control then maintaining an elevated temperature for the humidified gases where condensation may still form on the cold wall surfaces.

PTC material behaviour is exhibited in a range of polymer compositions with electrically conductive fillers. The behaviour can be characterised by a general statement that "providing certain other conditions are fulfilled, the composition becomes electrically conductive when particles of electrically conductive filler form a continuous chain, penetrating the material from the point of entry of electric current to the place where it leaves the polymer material". Polymer compositions containing electrically conductive filler can exhibit PTC properties due to the formation of a chain of filler particles that are close enough for current to flow at a certain temperature, generating heat which increases the temperature of the material until it reaches a phase transformation temperature. At the phase transformation temperature the crystalline polymer matrix changes to an amorphous structure. This change is accompanied by a small thermal expansion, forcing filler particles to move apart, breaking the conductive paths. Accordingly resistance rises sharply at this phase transformation temperature. As the material cools the small thermal conduction allows new conductive paths to form and current flow to resume. The rise and fall in temperature and the thermal contraction and expansion provides an inherent hysteresis in the cycle.

In producing a PTC material a number of factors have a bearing on the performance of the material. Particular factors include the quantity, type and particle size of the carbon black (or other conductive filler) used in the composite, the polymer that the carbon black binds with during mixing of the base materials and the process conditions such as temperature, pressure and time of mixing. It is important that the conductive filler particles are distributed evenly through the composite so that the composite exhibits uniform PTC behaviour.

For the present invention a PTC material having a phase transformation temperature not exceeding 40° C. is desired. One composition meeting these criteria has been developed and has the following composition:

20% by weight carbon black powder having a surface area of 254 m$^2$/g and oil Di-Butyl-Phthalate absorption of 188 cm$^3$/100 g. This powder is available as VULCAN XC-72 (powder) from Cabot Corporation.

64% Ethylene-Vinyl-Acetate. This material is available as ELVAX (grade 40 w) from Dupont (E.I. du Pont de Nemours and Company), with a density of 965 kg per m$^3$, a melting point of 46° C. and melting index of 52.

13.5% Plastomer. An example plastomer is available as EXACT 2M055 from ExxonMobil Corp, having a density of 882 kg/m$^3$, a melting point of 70° C. and a melting index of 3.

2.5% Wax.

This material was uniformly mixed and extruded to form a PTC ribbon with embedded conductors using a segmented screw extruder. The composite performance showed an acceptable level of self regulation without the temperature exceeding 40° C.

There are many possible ways of producing a tube having a PTC wall material with a pair of conductors running the length of the tube to have all of the potential pathways through the PTC material operating in parallel. A number of preferred embodiments are now described.

Figure 5:
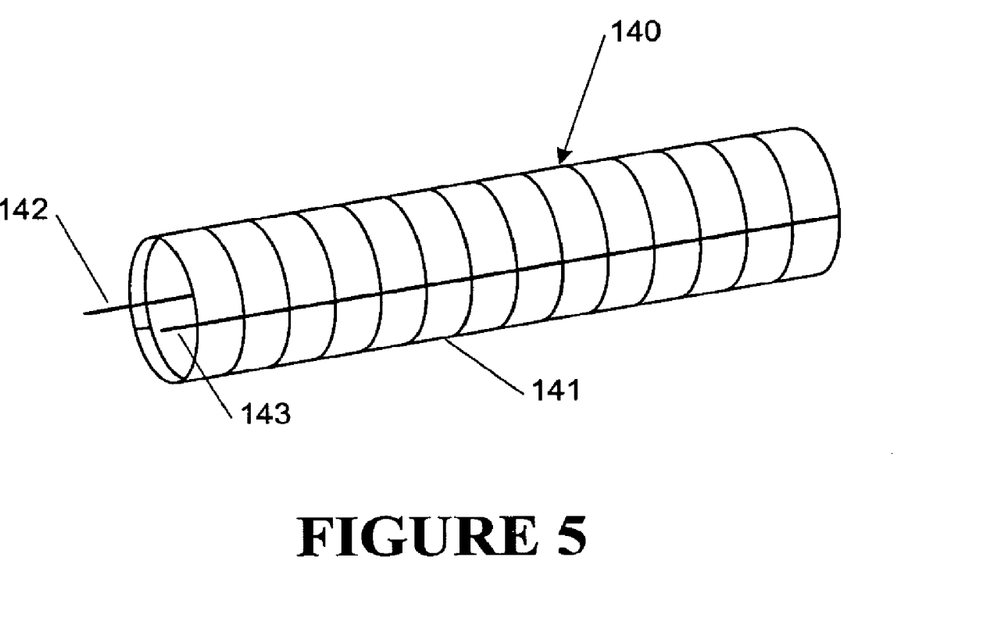
FIG. 5 is perspective view of a tube formed with a spirally wound PTC ribbon (without pre-embedded conductors) with longitudinally oriented conductors in the tube.

With reference to FIG. 5, a smooth walled tube 140 is shown by way of a first example. The smooth walled 140 tube has a PTC plastic material extruded as a narrow and thin ribbon 141 and wound helically with overlapping edges of adjacent turns. The edges of adjacent turns bind firmly to one another, fusing together in their molten state. A pair of conductors run 142, 143 longitudinally in the tube wall. The conductors are diametrically opposed. The conductors may be applied to either the internal or external surfaces of the molten PTC material during forming of the tube. To apply the conductors to the internal surface the conductors are applied longitudinally to the forming mandrel prior to laying the extruded PTC ribbon in place. Alternatively they may be applied directly to the outside of the PTC material while the material is still in a molten state. It can be appreciated that these conductors may also be applied helically rather than in a straight longitudinal direction, and that multiple conductors may be used.

Design of a PTC tube of this type involves selection of a wall thickness, a conductor gauge and a density of conductors in the PTC tube wall. The total resistance R(Ω) of the tube wall in its pre-threshold state will be a measure of the available power output for a given voltage. The available power output must be sufficient to offset the heat lose from the tube to its surrounding environment and (if the gases are entering the tube in a cooler state) to the humidified gases. The total resistance is proportional to the prethreshold volume resistivity X(Ωm) of the material and to the average shortest path distance between the conductors of opposite plurality. The total resistance is also proportional to the inverse of the length $L_C$ (m) of the conductors and to the inverse of the wall thickness t (m) of the PTC material. Furthermore, typically there will be a pair of opposite and alternate paths for current to flow from a conductor of one polarity to the conductor of the other polarity, halving the total resistance. Thus the total resistance can be found from the formula:

$$R = \frac{X\overline{w}}{2L_c t}$$

where $\overline{w}$(m) is the average shortest length path between conductors.

Therefore for a given tube length and diameter the total cold resistance may be varied by varying the density of conductors (varying the average shortest path distance between conductors) or by varying the wall thickness. The density of conductors may be varied by adding additional conductors in parallel (eg: a second or more pair of conductors) or by disposing the conductors in a helical arrangement with decreasing pitch corresponding to an increased density. For a given tube diameter D (m) and tube length $L_t$ (m) then the average shortest path length can be found using the total conductor path length for a single polarity (half the total conductor length) by:

$$\overline{w} = \frac{\pi D L_T}{2L_c}$$

The tube of FIG. 5 may be reinforced by applying a spiral bead, or by applying circumferential ribs to the outside of the tube, or by corrugating the tube, or by adding additional layers to the tube, particularly of a spiral ribbed or corrugated configuration, which would also provide additional external insulation from the ambient conditions.

Figure 6:
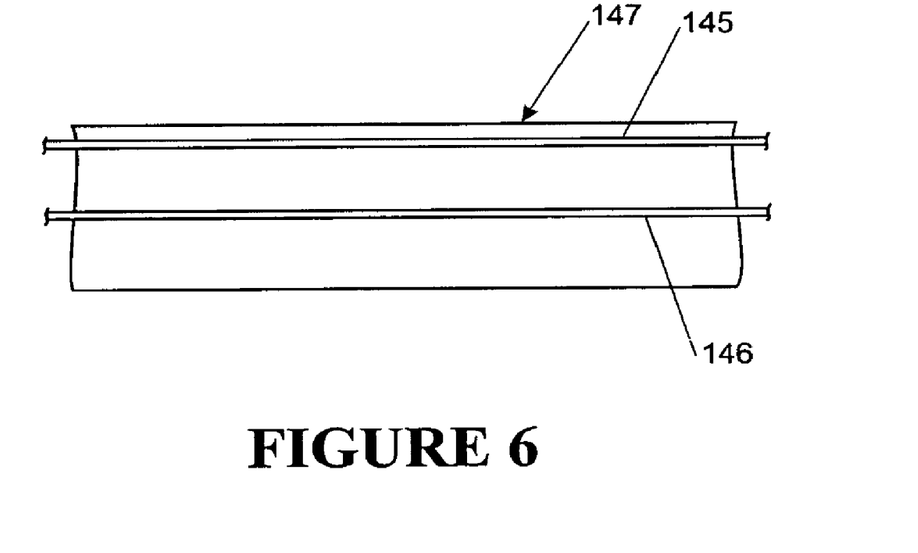
FIG. 6 is a plan view of a section of a ribbon of PTC material with a conductor embedded along one edge and second conductor embedded near the centre.
Figure 7:
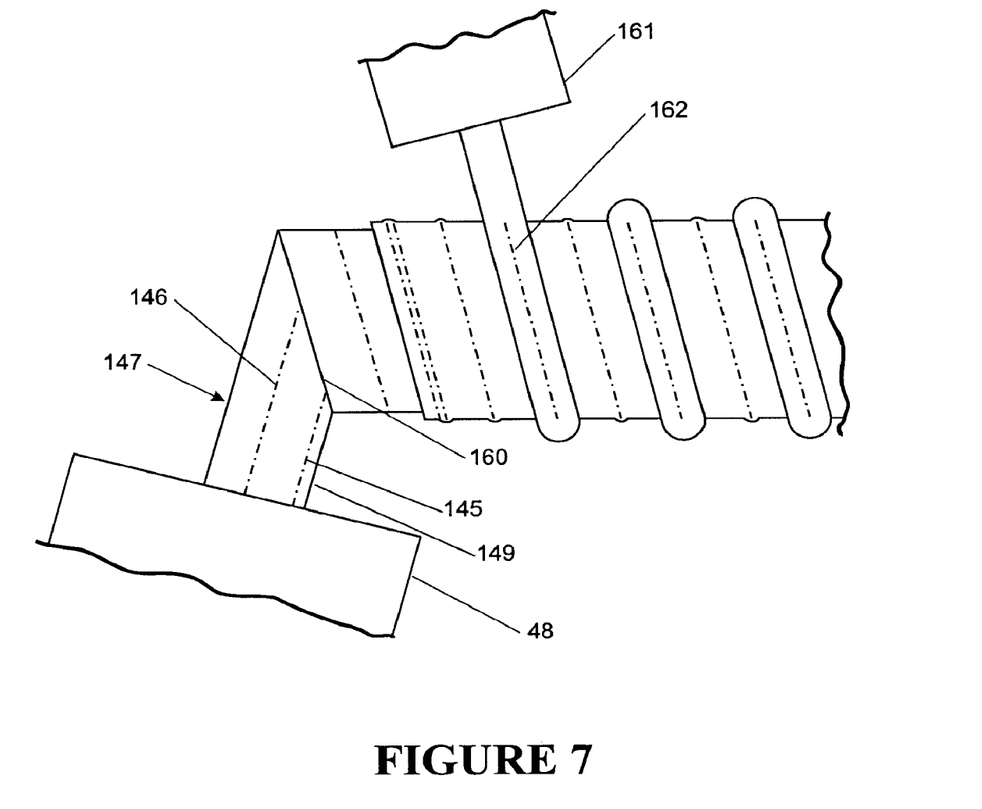
FIG. 7 is a plan view of a spiral forming arrangement performing a conduit using the ribbon of FIG. 6 (with the forming mandrel not shown).

A further construction is illustrated in FIGS. 6 and 7. FIG. 6 shows a pair of conductors 145, 146 extruded into a ribbon of PTC material. The first conductor 145 is disposed adjacent one edge of the PTC ribbon 147. The second conductor 146 is disposed adjacent the centre of the PTC ribbon 147. The exact location of the conductors within the PTC material is not critical, however the spacing between the conductors should be half of the pitch of winding the ribbon on to the former (eg: (width of ribbon−width of overlap between turns)÷2). For additional conductor density, additional pairs of conductors may be used. For lower conductor density the width of ribbon may be increased or alternatively a single conductor may be provided in the ribbon but two ribbons may be extruded and wound on to the former as a double helix.

Referring to FIG. 7 a manufacturing configuration is shown (without the rotating former, which may for example be a spiral pipeline mandrel available from OLMAS SRL of Italy). In this manufacturing configuration the PTC ribbon 147 is co-extruded with the embedded pair of conductors 145, 146 by a first extruder head 148. It is extruded directly on the former at a angle corresponding to the pitch of the former (the relationship between the advance and rotation speeds of tubes formed on it). The ribbon 147 is laid on the former so that the leading edge 149 of each new lap overlaps the trailing edge 150 of the immediately preceding turn. A reinforcing bead 162 is preferably extruded on to this overlap by an additional extruder head 161. The reinforcing bead 162 assists the bonding between overlapping turns of the ribbon as well as providing reinforcing against crushing of the formed tube.

Alternatively a conduit may be formed on a spiral pipeline mandrel with the reinforcing bead extruded to lie between the overlap of turns of the ribbon. This is particularly suited to where the ribbon is preformed and will not bond to itself without assistance. In this case contact may be provided between adjacent turns of the PTC ribbon along either side of the bead (for example by extended overlap) or the ribbon used may be have a conductor along each edge (as in FIG. 2).

Figure 8:
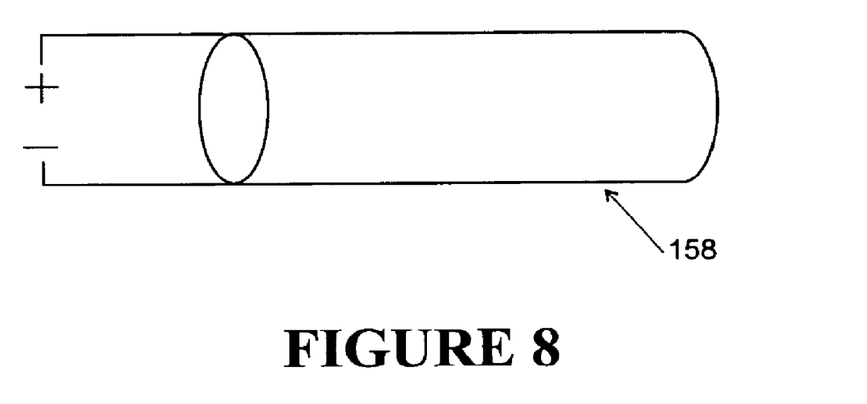
FIG. 8 shows construction of a tube incorporating flexible PTC elements in a parallel wire configuration.

FIG. 8 shows a further construction of a tube incorporating a parallel wire configuration. The tube 158 is a flexible PTC material, which has two conductors built into it.

The tube 158 according to this construction may be a directly extruded tube with the conductors co-extruded into the tube wall, or alternatively the conductors may be added subsequent to forming the tube by direct application to the exterior of the tube as wires or as conductive ink.

The tube may have an outer layer (not shown) which provides electrical insulation and thermal insulation to the tube.

The tube may be corrugated by passing through a set of corrugating rollers, to provide flexibility and lateral reinforcing against crushing.

The PTC design could also be extended to incorporate PTC heaters in other parts of the patient breathing circuit, such as the flexible extension tube which is usually connected between the Y-piece (port 17 of FIG. 1) and the patients endotracheal tube. A further extension of the PTC tube concept would be into a self-heated and temperature controlled endotracheal tube.

Figure 9:
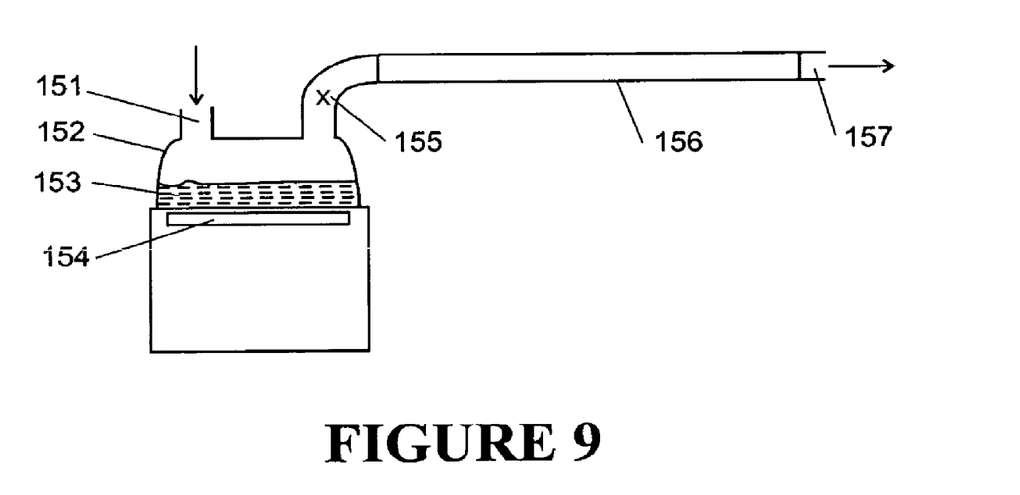
FIG. 9 shows a chamber combined with an unheated, well insulated delivery tube.

The tube with PTC wall material allows a humidifier to be used without any sensor at the patient airway. FIG. 9 shows a humidifier configuration using a PTC tube according to the embodiments of FIGS. 5 to 8. Gas enters humidification chamber 152 via inlet port 151 and is humidified by water 153, heated by heater plate 154. An absolute humidity sensor 155 controls the heater plate so that the gas passing sensor 155 is at a desired level of absolute humidity. PTC tube 156 is heated by an external voltage (not shown) so that the internal surface temperature is at a constant desired temperature, which is selected to be above the dewpoint of the gas. The gas which leaves tube 156 at outlet 157 will therefore be near the temperature of the tube, and containing the desired level of absolute humidity which was controlled by absolute humidity sensor 155.

The invention claimed is:

1. A humidification apparatus for use as part of a system for providing a humidified gases flow to a patient or other person in need of such gases comprising:
   a humidification chamber having an inlet and an outlet to allow said gases flow to pass through said humidification chamber, in use said humidification chamber partly filled with water, said inlet and said outlet above the surface of said water in use,
   a chamber heater provided adjacent said humidification chamber and adapted to heat and vaporise said water in said humidification chamber in order to provide water vapour to said gases flow passing through said humidification chamber,
   a gases transportation pathway connected to said outlet of said humidification chamber to convey said gases flow to said patient or other person in need of such gases,
   said gases transportation pathway comprising an open-ended thin-walled tube for transporting said humidified gases, said tube providing a self-supporting sealed path between each open end, said tube formed from positive temperature coefficient material, said positive temperature coefficient material formed so that it has a phase transformation temperature not exceeding 40° C., and also so that said pathway has a weight and flexibility suitable for the use of transporting gases from a medical humidifier to a patient, and
   at least one electrical conductor running the length of said tube and disposed in electrical contact with said positive temperature coefficient material,
   said tube corrugated along the length of said tube.

2. A humidification apparatus as claimed in claim 1, wherein the at least one electrical conductor is disposed helically within or on said wall of said gases transportation pathway, and is in conductive contact with said positive temperature coefficient material.

3. A humidification apparatus as claimed in claim 1, wherein at least two electrical conductors are disposed helically within or on said wall of said gases transportation pathway, and are in conductive contact with said positive temperature coefficient material, said helical disposition of said electrical conductors in said material is such that said electrical conductors are substantially evenly spaced from one another over their entire length.

4. A humidification apparatus as claimed in claim 1 wherein said at least two electrical conductors run longitudinally along the length of said tube, and each of said conductors is electrically connected with said positive temperature coefficient material.

5. A humidification apparatus as claimed in claim 4 wherein said at least two electrical conductors are diametrically opposed on said gases transportation pathway.

6. A humidification apparatus as claimed in claim 1 wherein said gases transportation pathway comprises a series of short conducting segments of tube connected in parallel.

7. A humidification apparatus as claimed in claim 1 wherein said gases transportation pathway is directly extruded.

\* \* \* \* \*